United States Patent
Suzuki

(10) Patent No.: US 9,823,182 B2
(45) Date of Patent: Nov. 21, 2017

(54) ELASTIC WAVE RECEIVING APPARATUS, ELASTIC WAVE RECEIVING METHOD, PHOTOACOUSTIC APPARATUS, AND PROGRAM

(75) Inventor: Koichi Suzuki, Kodaira (JP)

(73) Assignee: CANON KABUSHIKI KAISHA, Tokyo (JP)

(*) Notice: Subject to any disclaimer, the term of this patent is extended or adjusted under 35 U.S.C. 154(b) by 660 days.

(21) Appl. No.: 13/503,785

(22) PCT Filed: Dec. 9, 2010

(86) PCT No.: PCT/JP2010/072600
§ 371 (c)(1),
(2), (4) Date: Apr. 24, 2012

(87) PCT Pub. No.: WO2011/074618
PCT Pub. Date: Jun. 23, 2011

(65) Prior Publication Data
US 2012/0209104 A1 Aug. 16, 2012

(30) Foreign Application Priority Data
Dec. 15, 2009 (JP) .................................. 2009-284541

(51) Int. Cl.
*A61B 5/00* (2006.01)
*G01N 21/17* (2006.01)

(52) U.S. Cl.
CPC ....... *G01N 21/1702* (2013.01); *A61B 5/0091* (2013.01); *A61B 5/0095* (2013.01);
(Continued)

(58) Field of Classification Search
USPC .......................... 600/407, 476; 333/407, 476
See application file for complete search history.

(56) References Cited

U.S. PATENT DOCUMENTS 5,860,934 A * 1/1999 Sarvazyan .................... 600/587
6,190,334 B1 * 2/2001 Lasky .................. A61B 5/0053
600/587
(Continued)

FOREIGN PATENT DOCUMENTS

JP 2004-195088 7/2004

OTHER PUBLICATIONS

Dixon et al (Phase change measurement of ultrasound shear waves on reflection from a curing epoxy system, 2005).*
(Continued)

*Primary Examiner* — Joel F Brutus
(74) *Attorney, Agent, or Firm* — Fitzpatrick, Cella, Harper & Scinto

(57) ABSTRACT

An elastic wave receiving apparatus includes: a probe that receives an elastic wave generated from a subject; a plate-like compression plate that supports the subject and whose surface is scanned by the probe; a motor for driving the probe; a controller that supplies a drive signal to the motor so that the probe moves to a predetermined target position on the compression plate; and a load estimating unit that preliminarily acquires and stores a physical value corresponding to a load generated at the time of scanning the compression plate by the probe. The controller corrects the drive signal so that the probe moves to the target position regardless of the load by using the physical value stored in the load estimating unit.

24 Claims, 11 Drawing Sheets

(52) U.S. Cl.
CPC .......... *A61B 5/4312* (2013.01); *A61B 5/6843* (2013.01); *G01N 2021/1706* (2013.01)

(56) References Cited

U.S. PATENT DOCUMENTS

| | | | |
|---|---|---|---|
| 6,950,693 B1* | 9/2005 | Wehberg .................... | 600/476 |
| 2005/0113683 A1* | 5/2005 | Lokhandwalla ..... | A61B 5/0091 600/427 |
| 2008/0101537 A1* | 5/2008 | Sendai .................. | A61B 6/025 378/23 |
| 2008/0208044 A1* | 8/2008 | Lecoq .................. | A61B 8/0825 600/436 |
| 2011/0231160 A1 | 9/2011 | Suzuki ......................... | 702/189 |

OTHER PUBLICATIONS

S. Manohar et al., "Region-of-Interest Breast Studies Using the Twente Photoacoustic Mammoscope (PAM)", *Proc. of SPIE*, vol. 6437, pp. 643702-1-643702-9 (2007).

S. Manohar et al., "The Twente Photoacoustic Mammoscope: System Overview and Performance", *Physics in Medicine and Biology*, vol. 50, No. 11, pp. 2543-2557 (2005), XP020084213.

* cited by examiner

ELASTIC WAVE RECEIVING APPARATUS, ELASTIC WAVE RECEIVING METHOD, PHOTOACOUSTIC APPARATUS, AND PROGRAM

TECHNICAL FIELD

The present invention relates to an elastic wave receiving apparatus, an elastic wave receiving method, a photoacoustic apparatus and program.

BACKGROUND ART

In recent years, an apparatus for receiving an elastic wave generated from the inside of a subject by a probe and imaging the structure of the inside is being studied and developed. As one of applications, a photoacoustic diagnostic apparatus that irradiates the inside of a subject with a laser beam, receives a photoacoustic wave generated from the inside of the subject by an ultrasound probe, and displaying a tissue image of the inside of the subject is proposed (refer to, for example, NPL1). In an example of the photoacoustic diagnostic apparatus, a subject (breast) is compressed by plates and an ultrasound probe and irradiated with a pulse laser beam over the plate. A photoacoustic wave generated on the inside of the subject is received by the ultrasound probe, and a tissue image of the inside of the subject is reconstructed and displayed. A two-dimensional scanning mechanism capable of performing a two-dimensional scan by the probe and a pulse laser generator facing the probe to obtain a tissue image of the entire subject (breast) is provided, and a photoacoustic wave is measured in a plurality of measurement points.

An ultrasonic diagnosis apparatus having a mechanism of performing a mechanical scan by a probe and a method for controlling the same are known (refer to, for example, PTL1). In the ultrasonic diagnosis apparatus, the probe is provided with a position detector, a speed signal is generated from a position signal, and the difference between a target position and target speed is fed back to a drive signal of the probe.

In those diagnosis apparatuses, at the time of receiving a photoacoustic wave or ultrasound generated in the subject by the probe, when there is a space between the subject and the probe, the picture quality of a tissue image of the part deteriorates markedly for the following reason. The acoustic impedance of air in the space and that of the subject are largely different from each other, and the ultrasonic wave hardly passes through the space. To avoid the issue, a matching agent whose acoustic impedance is close to that of the subject is inserted between the probe and the subject so as not to have a space. To prevent a space from being created at the time of performing a mechanical scan by the probe, the probe, the subject, and the plates have to be sufficiently closely attached to each other so as not to have a space.

CITATION LIST

Patent Literature

PTL 1: Japanese Patent Application Laid-Open No. 2004-195088

Non Patent Literature

NPL 1: Srirang Manohar, et. al: Region-of-interest breast studies using the Twente Photoacoustic Mammoscope (PAM), Proc. of SPIE, Vol. 6437, pp. 1-9, 2007.

SUMMARY OF INVENTION

Technical Problem

However, in a conventional photoacoustic diagnosis apparatus, a subject is compressed by plates and a matching agent is applied measurement by measurement. At this time, there is a case that a load at the time of moving the probe over the plate fluctuates due to individual difference of the subject, strain of the plates, scratch, an application state of a matching agent, fluctuations in atmosphere temperature, and the like. Consequently, due to the load fluctuations, there is a case that the position of the probe upon reception of the photoacoustic wave is deviated from the target position, and the precision of the reconstructed tissue image deteriorates. In the case where the load on the probe at the time of movement over the plate becomes large and the position of the probe is markedly deviated, measurement has to be started again, and it requires extra laser beam application to the subject. There is an issue that the stress on the patient increases. Further, to drive the probe accurately to the target position in spite of a large load, an actuator of larger capacity is necessary, and an issue occurs such that cost reduction of the apparatus is hindered.

The present invention has been devised in consideration of the situations of the conventional arts as described above. An object of the present invention is to provide an elastic wave receiving apparatus and an elastic wave receiving method realizing increased position precision of a probe without increasing cost even in a situation that the load on the probe at the time of movement over a plate fluctuates.

Solution to Problem

An elastic wave receiving apparatus according to this invention comprising:

a plate-like member that supports a subject in a supporting side as one of faces;

a probe that receives an elastic wave generated from the subject by scanning a scanning side as the other side of the supporting side of the plate-like member;

a driving unit that drives the probe so as to scan the scanning side of the plate-like member;

a drive controlling unit that supplies a drive signal to the driving unit so that the probe moves to a predetermined target position on the scanning side; and an information acquiring unit that preliminarily acquires and stores a physical value corresponding to a load generated in the driving unit when the scanning side is scanned by the probe, wherein the drive controlling unit corrects the drive signal so that the probe moves to the target position regardless of the load by using the physical value stored in the information acquiring unit.

An elastic wave receiving method according to this invention for making a probe scan a plate-like member that supports a subject by an instruction signal to move the probe to a predetermined target position, and receiving an elastic wave generated from the subject by the probe, comprising:

an information acquiring step of preliminarily acquiring a physical value corresponding to a load necessary to move the probe, over the plate-like member;

an instruction signal correcting step of correcting the instruction signal by using the physical value acquired in the information acquiring step; and a driving step of moving the probe to the target position by the instruction signal corrected in the instruction signal correcting step.

Advantageous Effects of Invention

According to the present invention, by estimating a load at the time of making a probe scan the surface of a plate-like member and changing a driving method so that the probe can move to a target position, the position precision of the probe can be increased and the precision of a tissue image can be improved without increasing cost.

Further features of the present invention will become apparent from the following description of exemplary embodiments with reference to the attached drawings.

DESCRIPTION OF EMBODIMENTS

Embodiments for carrying out the present invention will be illustratively and specifically described below with reference to the drawings.

EXAMPLE 1

Figure 1:
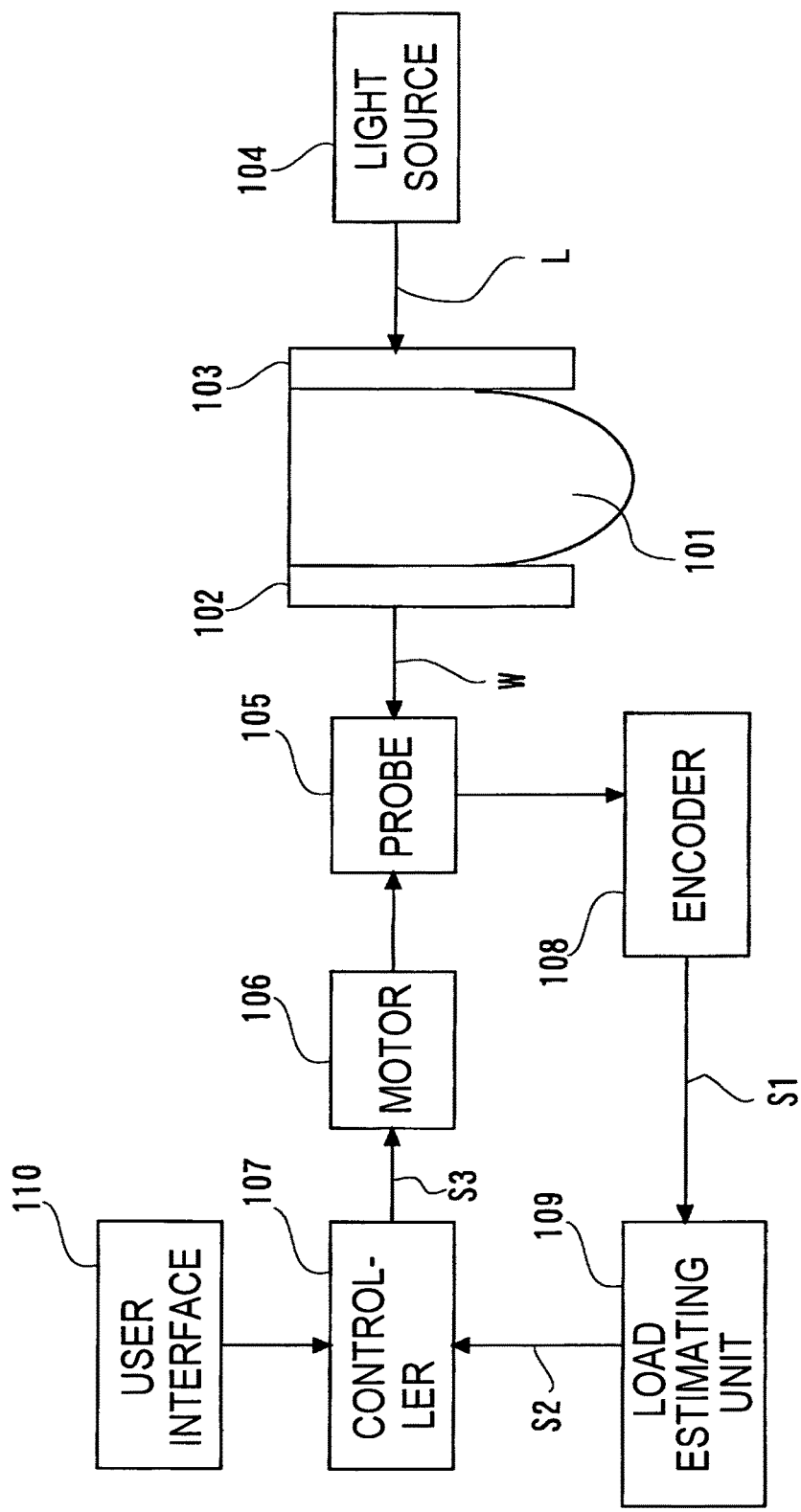
FIG. 1 is a block diagram of an elastic wave receiving apparatus according to a first embodiment of the invention.

FIG. 1 is a block diagram showing a schematic configuration of an elastic wave receiving apparatus according to the embodiment. In FIG. 1, a configuration other than a light source 104 corresponds to an elastic wave receiving apparatus, and a configuration including the light source 104 corresponds to a photoacoustic apparatus. In FIG. 1, 101 denotes a breast as a subject. The subject 101 is supported by being sandwiched and compressed by compression plates 102 and 103 each having a plate-like shape as a plate-like member. The compression plate 102 compresses and supports the subject by its supporting side as one of sides. In this state, a laser beam L for making the subject 101 generates a photoacoustic wave is emitted from the pulse laser light source 104. The pulse laser light source 104 irradiates the subject 101 with the laser beam L while making the laser beam L fluctuate in pulses at predetermined frequency. A photoacoustic wave generated when energy of the emitted laser beam is absorbed by the subject 101 and diffused is received as an elastic wave W by a probe 105 and converted to an electric signal. By being driven by a motor 106 as a driving unit, the probe 105 can two-dimensionally scan the surface of the scanning side as the opposite side of the supporting side of the compression plate 102 in the entire subject 101.

The motor 106 is a pulse motor, which is driven by a pulse signal S3 generated by a controller 107 as a drive controller, and the driving of the motor 106 is controlled according to the number and frequency of the pulse signals S3 output from the controller 107. Concretely, the rotational angle of the motor 106 changes in proportion to the number of pulse signals S3. The rotation speed of the motor 106 changes in proportion to the frequency of the pulse signal S3. That is, by controlling the number and frequency of the pulses output from the controller 107, the position, speed, and acceleration of the probe 105 can be controlled. The position information on the compression plate 102 of the probe 105 is acquired by an encoder 108 as a position detecting unit.

Position information S1 of the probe 105 acquired by the encoder 108 is transmitted to a load estimating unit 109 as an information acquiring unit. In the load estimating unit 109, an estimation value corresponding to a load at the time of making the probe 105 move over the compression plate 102 is calculated based on the position information S1 of the probe 105 and stored. The load estimating unit 109 includes a microcontroller (or computer) and software (or a program) assembled in the microcontroller. An estimation value S2 corresponding to the load calculated by the load estimating unit 109 is transmitted to the controller 107. The controller 107 has the function of changing the number and timing of the drive pulse signals of the motor 106 based on the transmitted estimation value S2. A user interface 110 is an interface used by the operator to perform an operation start instruction of the elastic wave receiving apparatus, an end instruction, reception data viewing, and the like.

Figure 2:
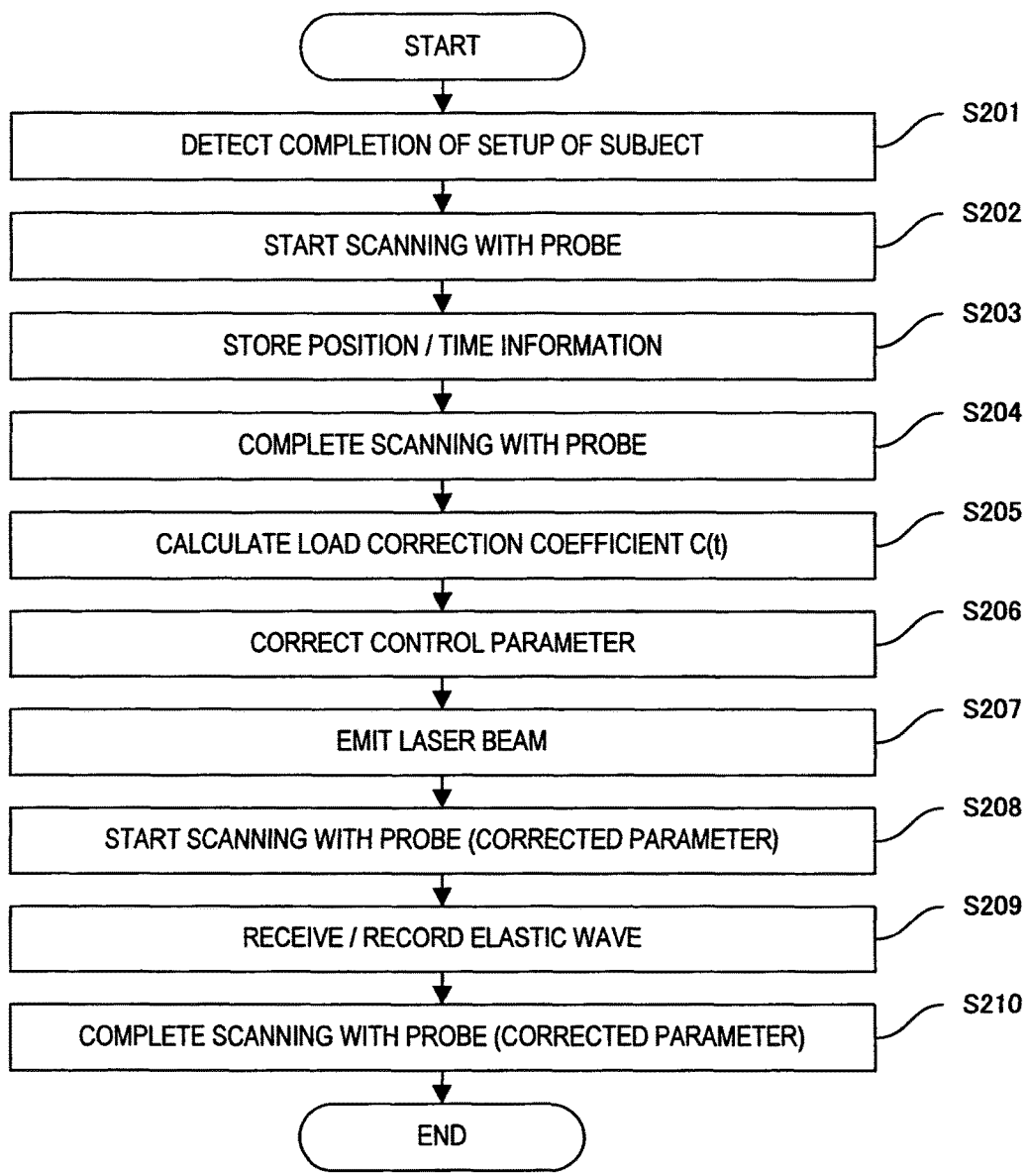
FIG. 2 is a flowchart showing a measurement flow according to the first embodiment of the invention.

FIG. 2 shows a measurement flow since the subject 101 is supported by being compressed by the compression plates 102 and 103 until an elastic wave is received/recorded by the probe 105 in the case where the elastic wave receiving apparatus according to the embodiment is used. When the measurement flow starts, first, in step S201, the subject 101 is compressed/supported by the compression plates 102 and 103, and completion of setup of the subject 101 is detected. Concretely, the operator performs a series of preparations such as compression of the subject 101, fixing, and application of the matching agent and, after that, transmits an operation start instruction signal to the controller 107 via the user interface 110. By detecting the operation start instruction signal by the controller 107, completion of setup of the subject 101 is detected.

Figure 3:
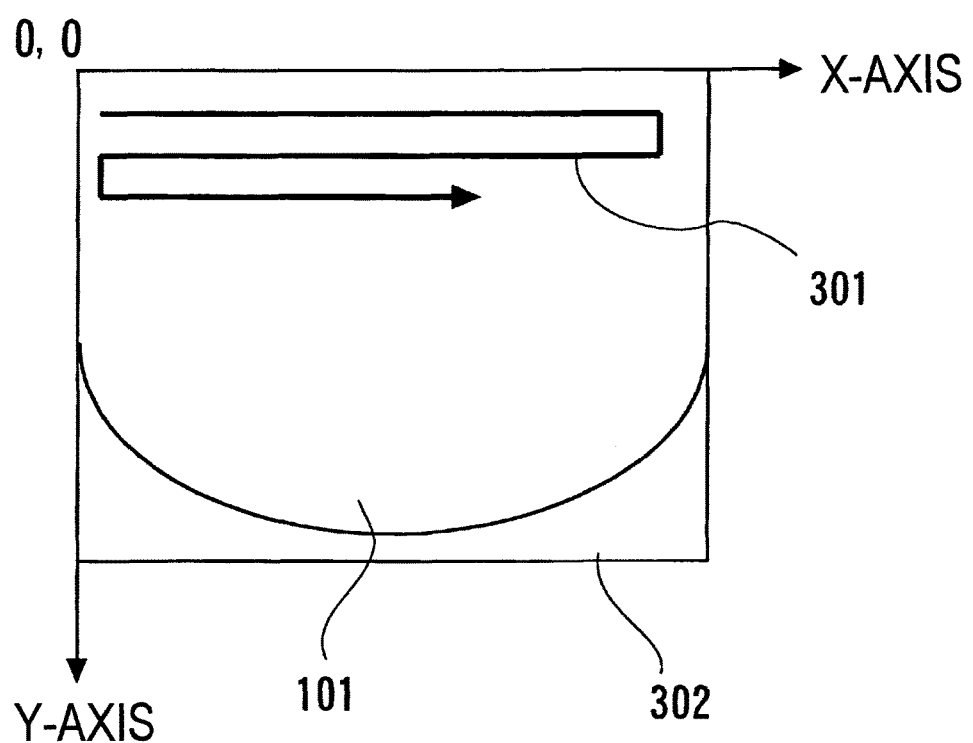
FIG. 3 is a diagram showing a mode of a scan of a probe according to the first embodiment of the invention.

In step S202, the controller 107 generates a motor drive signal based on a predetermined target position at each time of the probe 105 to start a scan of the probe 105. The details of the scan of the probe 105 will now be described with reference to FIGS. 3 and 4. FIG. 3 is a diagram when the subject 101 and the compression plate 102 are seen from the direction of the probe 105. In FIG. 3, 302 indicates a scan region as a region to be scanned in the subject 101 by the probe 105. In FIG. 3, the left upper corner in the diagram of the scan region 302, a right-pointing axis in the horizontal direction is defined as X axis, and a down-pointing axis in the perpendicular direction is defined as Y axis. In the embodiment, the controller 107 makes the probe 105 scan the scan region 302 in a pattern indicated by an arrow 301.

For simplicity, the case where the probe 105 performs a scan once in the X axis direction will be assumed and described.

Figure 4:
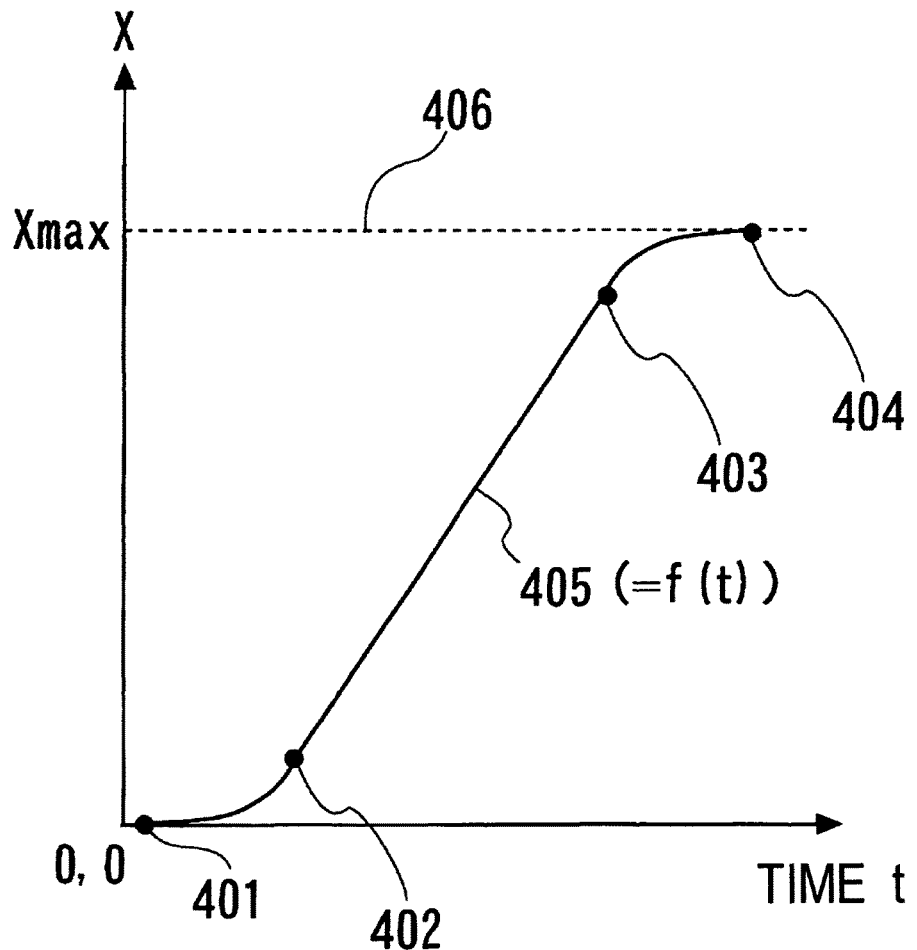
FIG. 4 is a diagram showing the relation between a target position of the probe and time.

FIG. 4 is a diagram showing a target position f(t) at each predetermined time. In the diagram, time at which the operator gives the measurement start instruction is set as "0", and the horizontal axis indicates time "t". The vertical axis indicates the horizontal position X of the probe 105. The target position f(t) of the probe 105 in each time is expressed by a solid line 405. In f(t), at time of a point 401, the probe 105 starts moving at time indicated by the point 401 and accelerates at constant acceleration until time indicated by a point 402. After that, the probe 105 moves at constant speed until time indicated by a point 403 and decelerates at constant acceleration until time indicated by a point 404. At the time indicated by the point 404, the probe 105 reaches the right end of the scan region.

Description of the measurement flow of FIG. 2 will be continued. The target position f(t) of the probe 105 at each time is calculated in advance at predetermined time intervals "dt" and stored in an internal memory of the controller 107. The number N(t) of pulses, which are input from the controller 107 to the motor 106 from time "t" to time "t+dt" in step S202, is calculated by the following expression (1).

[Math. 1]

$$N(t) = \frac{f(t+dt) - f(t)}{p} \quad (1)$$

where the amount of movement of the probe 105 performed in response to input of the pulse signal once to the motor 106 is expressed as "p".

In actual elastic wave measurement, the scan is repeated along the pattern 301, and the entire scan region 302 is scanned with the probe 105. When the scan of the probe 105 starts, in step S203, the position data of the probe 105 is acquired at predetermined time intervals by using the encoder 108. The position data and data indicative of the time is input to the load estimating unit 109.

Figure 5:
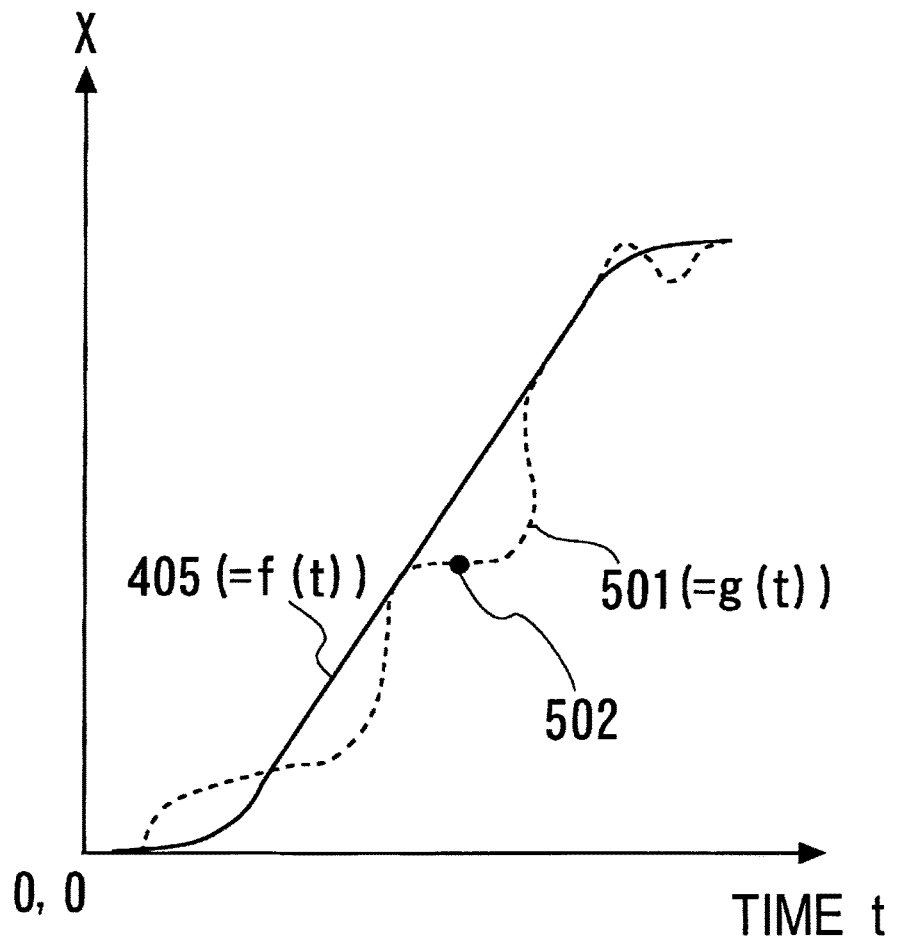
FIG. 5 is a diagram showing the relation between a measurement position of the probe and time.

During a scan of the probe 105, the process in step S203 is continued. After completion of the scan of the probe 105 in step S204, in subsequent step S205, a load (necessary for movement) at the time of moving the probe 105 over the compression plate 102 is estimated by the load estimating unit 109. The load estimating unit will be described in detail by using FIG. 5. In FIG. 5, the solid line 405 indicates the target position f(t) of the probe 105. A broken line 501 indicates the actual position of the probe 105 measured in step S203. In a place where the value of X of the broken line 501 is larger than the value of X at the same time indicated by the solid line 405, it is determined that the load at the time of moving the probe 105 over the compression plate 102 is smaller than an assumed value. On the other hand, in a place where the value of X of the broken line 501 is smaller than the value of X at the same time indicated by the solid line 405, it is determined that the load at the time of making the probe 105 scan the surface of the compression plate 102 is larger than an assumed value.

It is understood that, for example, around the point 502 shown in FIG. 5, the tilt of the actual position 501 of the probe 105 decreases and is deviated from the target position 405. It shows that the load at the time of moving the probe 105 over the compression plate 102 increases around the point 502 and the probe 105 cannot be accurately moved to a target position at each time by the position control of the probe 15 executed in step S202. To address the situation, in the embodiment, a load correction function C(t) is calculated and, by using the load correction function C(t), the position of the probe 105 is corrected. The actual measurement position of the probe 105 at time "t" shown by the broken line 501 is expressed as g(t), "k" is set as a predetermined positive constant, and the load correction function C(t) is defined as the following expression (2).

[Math. 2]

$$C(t) = k\{f(t) - g(t)\} \quad (2)$$

For example, around the point 502, the load correction function C(t) is a positive value.

After completion of the process in step S205, subsequently in step S206, the load estimating unit 109 changes the driving method (control parameter) on the motor 106 based on the load correction function C(t) and sets it in the controller 107. In the embodiment, it is assumed that a value obtained by adding the load correction function C(t) to the input number N(t) of pulses every time interval dt which is preliminarily set is set as a corrected pulse input number N'(t). The controller 107 re-calculates the corrected pulse input number N'(t) at time interval dt to update the data in the memory in the controller 107.

After completion of the process in step S206, subsequently in step S207, control of making a pulse laser beam emitted from the light source 104 repeatedly in predetermined cycles starts. In step S208 subsequent to the process in step S207, the controller 107 starts the driving of the motor 106 (and the probe 105) by using the corrected pulse input number N'(t). Simultaneously, the light source 104 is driven so as to be opposed to the probe 105, and a photoacoustic wave generated in the subject 101 by the pulse laser beam is received by the probe 105.

For example, around the point 502, the controller 107 makes pulse signals generated more than the first pulse input number N(t) based on the corrected pulse input number N'(t) so that the probe 105 can follow the target position f(t). Consequently, also in the case where the load at the time of movement of the probe 105 increases around the point 502, the actual position of the probe 105 at each time can be made closer to the first target position f(t). When the scan of the probe 105 starts in step S208, in step S209, control of receiving a photoacoustic wave generated from the inside of the subject 101 by the probe 105 and converting it to an electric signal is executed. The electric signal is subjected to signal processing and imaging by another routine (not shown), and an image may be displayed in the user interface 110. Until the probe 105 reaches the right end Xmax of the scan region, the movement of the probe and the reception of the photoacoustic wave are performed repeatedly. When the probe 105 reaches the right end Xmax of the scan region, the scan of the probe is finished in step S210 and reception and recording of the elastic wave is also finished.

In the measurement flow, the processes in step S202 to S204 correspond to an information acquiring step. The processes in steps S205 and S206 correspond to an instruction signal correcting step. Further, the processes in steps S208 to S210 correspond to a driving step. The pulse input number N(t) corresponds to an instruction signal. For example, in the case where coefficient of friction in a part of the compression plate 102 is low and the load is small, the controller 107 generates pulse signals of the number smaller than the initial pulse input number N(t) based on the corrected pulse input number N'(t). In such a manner, the probe 105 can follow the target position f(t). Therefore, also in the case where the load at the movement of the probe 105 is small, the actual position of the probe 105 at each time can be made closer to the initial target position f(t).

In the above example, the case where a scan is performed once in the X direction in FIG. 3 by the probe 105 has been described. However, in reality, the value of the target position f(t) also on each Y coordinate is stored and the corrected pulse input number N'(t) is calculated at each Y coordinate by a similar method. In such a manner, variations in each place of the load at the time of moving the probe 105 over the compression plate 102 can be corrected in the entire scan region 302. Although the expression in which the difference between the measurement position and the target position is multiplied by a positive constant is used as the load correction function C(t) in the above example, the load correction function C(t) is not always limited to the expression. Another function which changes according to the difference between the measurement position and the target position may be used. In the embodiment, the difference between the measurement position and the target position corresponds to a physical value corresponding to the load generated in the driving unit.

In the embodiment, as a corrected pulse input number, an expression of adding a pulse input number before correction and the load correction function C(t) is used. However, the invention is not always limited to the expression. Another function which changes according to the value of the load correction function C(t) may be used. In the embodiment, the method in which the acceleration start time is the same regardless of the load correction function C(t) has been described. However, the acceleration start time may be also changed. For example, in the case where the load is estimated large, a driving method is changed so as to increase the pulse input number and hasten the timing of the pulse input (increase the drive speed and hasten the drive timing (or increase movement speed and hasten moving timing)). In such a manner, the probe can be moved to a target position before generation of a photoacoustic wave. On the other hand, for example, in the case where the load is estimated small, a driving method is changed so as to decrease the pulse input number and delay the timing of the pulse input (decrease the drive speed and delay the drive timing (or decrease the movement speed and delay the moving timing)). In such a manner, the probe can be moved to a target position.

Although the embodiment has been described by using the example that the motor 106 is a pulse motor, the invention is not limited to the kind of the motor. A motor of another kind such as a servo motor may be used as long as the position and speed can be controlled from the controller 107.

EXAMPLE 2

Figure 6:
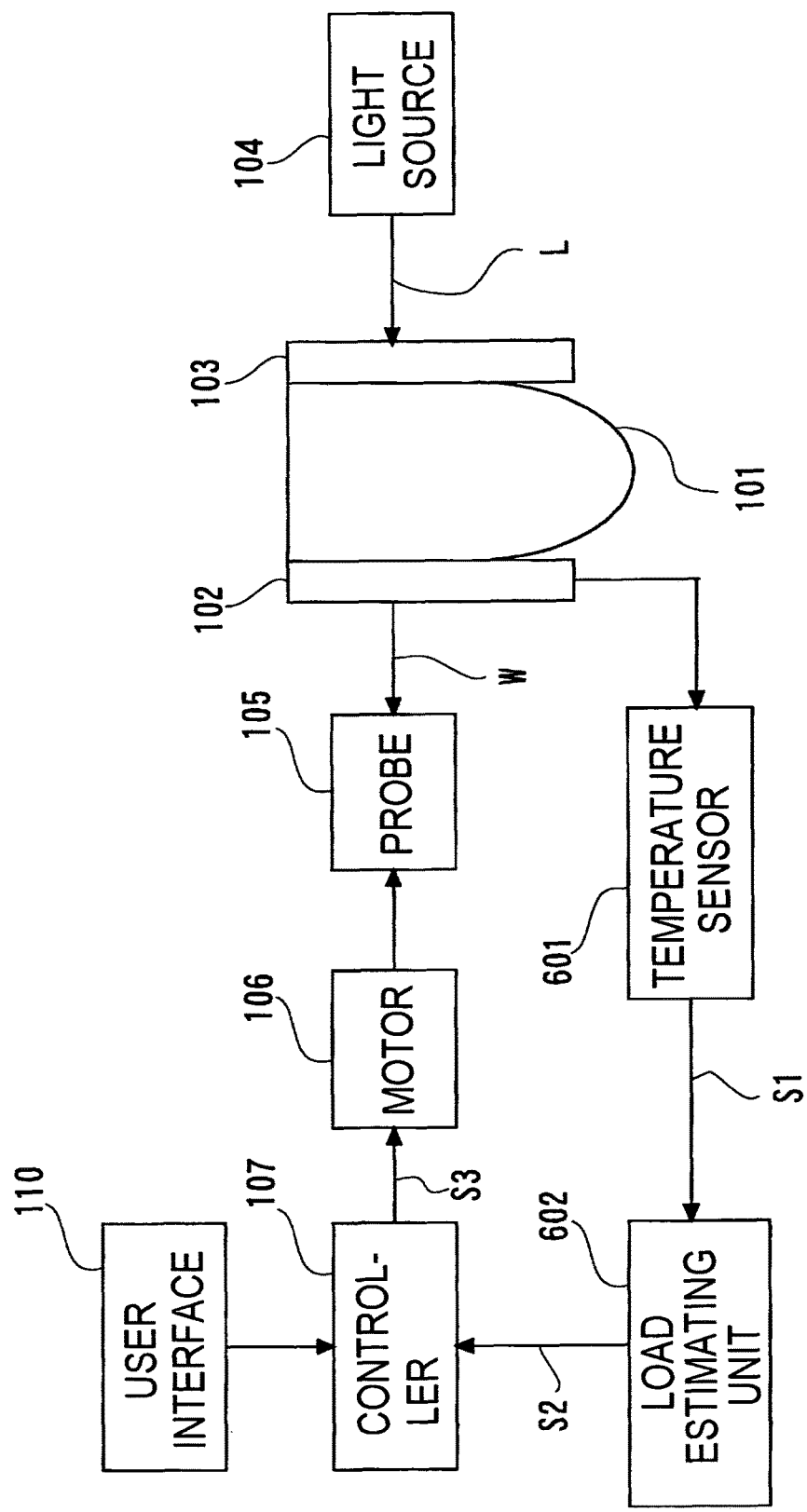
FIG. 6 is a block diagram of an elastic wave receiving apparatus according to a second embodiment of the invention.
Figure 7:
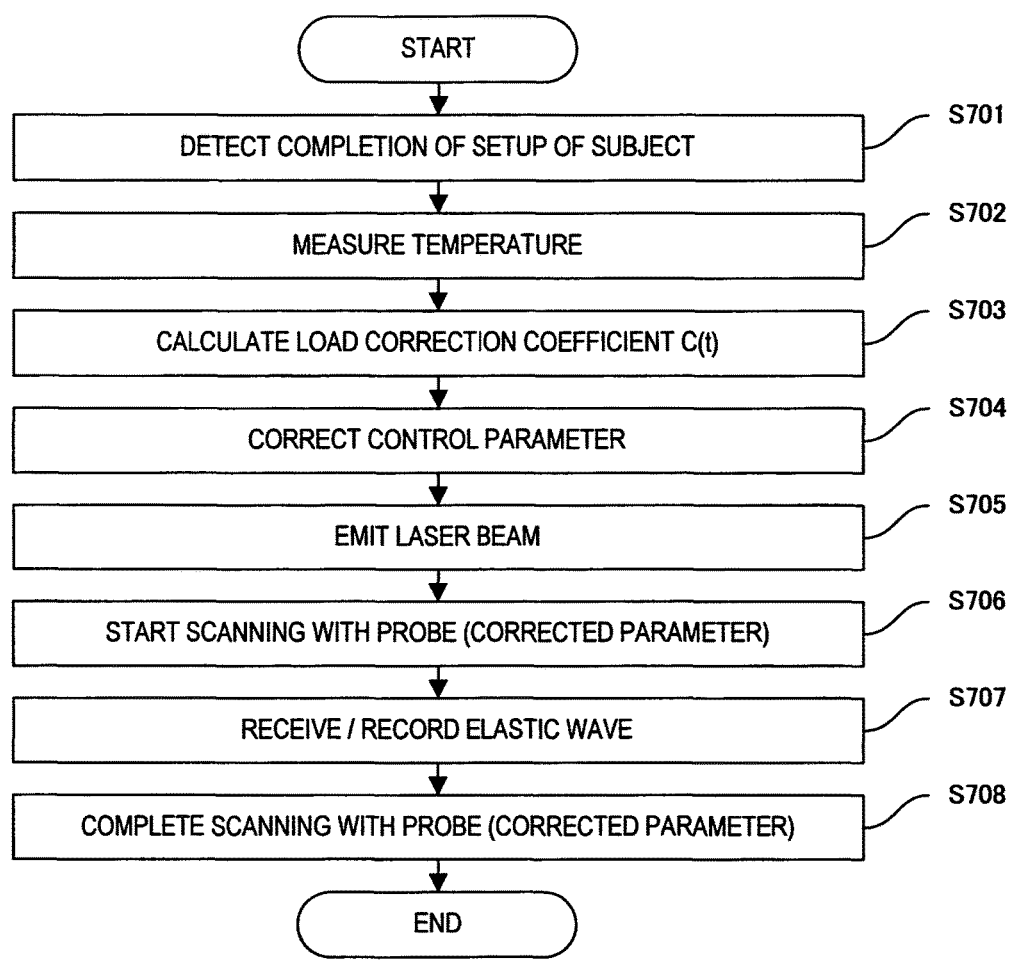
FIG. 7 is a flowchart showing a measurement flow according to the second embodiment of the invention.

FIG. 6 is a block configuration diagram showing a second embodiment of an elastic wave receiving apparatus according to the present invention. In the elastic wave receiving apparatus of the embodiment, to correct variations in the load in association with movement of the probe 105 due to temperature fluctuations, a temperature sensor 601 and a load estimating unit 602 are provided. In FIG. 6, the subject 101, the compression plate 102, the compression plate 103, the light source 104, the probe 105, the motor 106, the controller 107, and the user interface 110 are similar to those in the first embodiment, so that their description will not be repeated. FIG. 7 shows a measurement flow using the elastic wave receiving apparatus since the subject 101 in the second embodiment of the invention is sandwiched, compressed, and supported by the compression plates 102 and 103 until an elastic wave is received by the probe 105.

In step S701, the operator performs a series of preparations such as compression of the subject 101, fixing, and application of the matching agent and, after that, transmits an operation start instruction signal to the controller 107. When the operation start instruction signal is detected by the controller 107, completion of setup of the subject 101 is detected. In step S702, the temperature of the compression plate 102 is measured by the temperature sensor 601 as a temperature detecting unit. A thermistor element is adhered onto the compression plate 102, and the temperature of the compression plate 102 is measured from a resistance value of the thermistor element. Subsequently, in step S703, the load estimating unit 602 estimates the load related to movement of the probe 105 based on the target position f(t) indicated by the solid line 405 in FIG. 4 and temperature T measured in step S702.

When viscosity at the temperature T of the matching agent is set as u(T), a load D(t) by viscous property of the matching agent when the probe 105 moves over the compression plate 102 is proportional to viscosity and speed. The speed is obtained by time-differentiating f(t). That is, the load D(t) is estimated by the following expression (3) using u(T) and f(t).

[Math. 3]

$$D(t) = u(T)\frac{f(t+dt) - f(t)}{dt} \quad (3)$$

The load correction function C(t) is calculated by the following expression (4). "k" denotes a constant which is pre-stored internally.

[Math. 4]

$$C(t) = kD(t) \quad (4)$$

Generally, the lower the temperature T is, the larger the load D(t) by the viscous property of the matching agent becomes. When the load D(t) by the viscous property of the matching agent is large, the load correction function C(t) also becomes a large value.

In step S704, the load estimating unit 109 changes the target position based on the load correction function C(t) and sets it in the controller 107. In the embodiment, a value obtained by adding the load correction function C(t) to the predetermined pulse input number N(t) is set as a corrected pulse input number N'(t). The controller 107 re-calculates the corrected pulse input number N'(t) at time intervals dt and updates the internal memory. Subsequently, in step S705, control of repeatedly emitting a pulse laser from the light source 104 in predetermined cycles is started. In the following step S706, the controller 107 starts driving the motor 106 and the probe 105 by using the corrected pulse input number N'(t). Concurrently, the light source 104 is also driven so as to face the probe 105 so that a photoacoustic wave generated on the inside of the subject 101 by the pulse laser beam can be received by the probe 105.

For example, in the case where it is expected that the temperature of the compression plate 102 is low and the load related to movement of the probe 105 is large, the controller 107 generates pulse signals more than the initial pulse input number N(t) based on the corrected pulse input number N'(t) so that the probe 105 can follow the target position f(t).

Consequently, also in the case where the load related to movement of the probe 105 increases due to low temperature, the position and time of the probe 105 can be made closer to the target position f(t). For example, in the case where it is expected that the temperature of the compression plate 102 is high and the load related to movement of the probe 105 is small, the controller 107 generates pulse signals smaller than the first pulse input number N(t) based on the corrected pulse input number N'(t) so that the probe 105 can follow the target position f(t). Consequently, also in the case where the load related to movement of the probe 105 decreases due to high temperature, the position and time of the probe 105 can be made closer to the target position f(t).

Subsequently, in step S707, control of receiving a photoacoustic wave generated from the inside of the subject 101 by the probe 105 and converting it to an electric signal is executed. The electric signal may be subjected to signal processing and imaging on the outside and an image may be displayed in the user interface 110. In step S708, the scan with the probe 105 and reception of the elastic wave is finished. In the measurement flow, the process in step S702 corresponds to an information acquiring step. The processes in steps S703 and S704 correspond to an instruction signal correcting step. Further, the processes in steps S706 to S708 correspond to a driving step. The pulse input number N(t) corresponds to an instruction signal.

As described above, according to the second embodiment of the invention, fluctuations in the load related to movement of the probe 105 accompanying temperature fluctuations can be estimated by a simple method without making the probe 105 scan before measurement. Consequently, without increasing the measurement time, the load fluctuations accompanying temperature fluctuations are corrected, and the position precision of the probe 105 can be improved. Although the expression in which a product of viscosity and speed is multiplied by a positive constant is used as the load correction function C(t) in the above example, the load correction function C(t) is not always limited to the expression. Another function which changes according to temperature may be used. Although the expression in which the pulse input number N(t) before correction and the load correction function C(t) are added is used as the corrected pulse input number N'(t) in the embodiment, the invention is not always limited to the expression. Another function which changes according to the value of the load correction function C(t) may be used. In the embodiment, the temperature of the compression plate 102 corresponds to the physical value corresponding to the load generated in the driving unit.

In the embodiment, the method in which the acceleration start time of the probe 105 is the same regardless of the load correction function C(t) has been described. However, the acceleration start time may be also changed together with a change in the number of input pulses. For example, in the case where the load related to movement of the probe 105 is estimated large, a driving method is changed so as to increase the pulse input number and hasten the timing of the pulse input (increase the drive speed and hasten the drive timing (or increase the movement speed and hasten the moving timing)). In such a manner, the probe 105 can be moved to a target position well in advance of generation of a photoacoustic wave. On the other hand, for example, in the case where the load related to movement of the probe 105 is estimated small, a driving method is changed so as to increase the pulse input number and delay the timing of the pulse input (decrease the drive speed and delay the drive timing (or decrease the movement speed and delay the moving timing)). In such a manner, the probe 105 can be moved to a target position.

EXAMPLE 3

Figure 8:
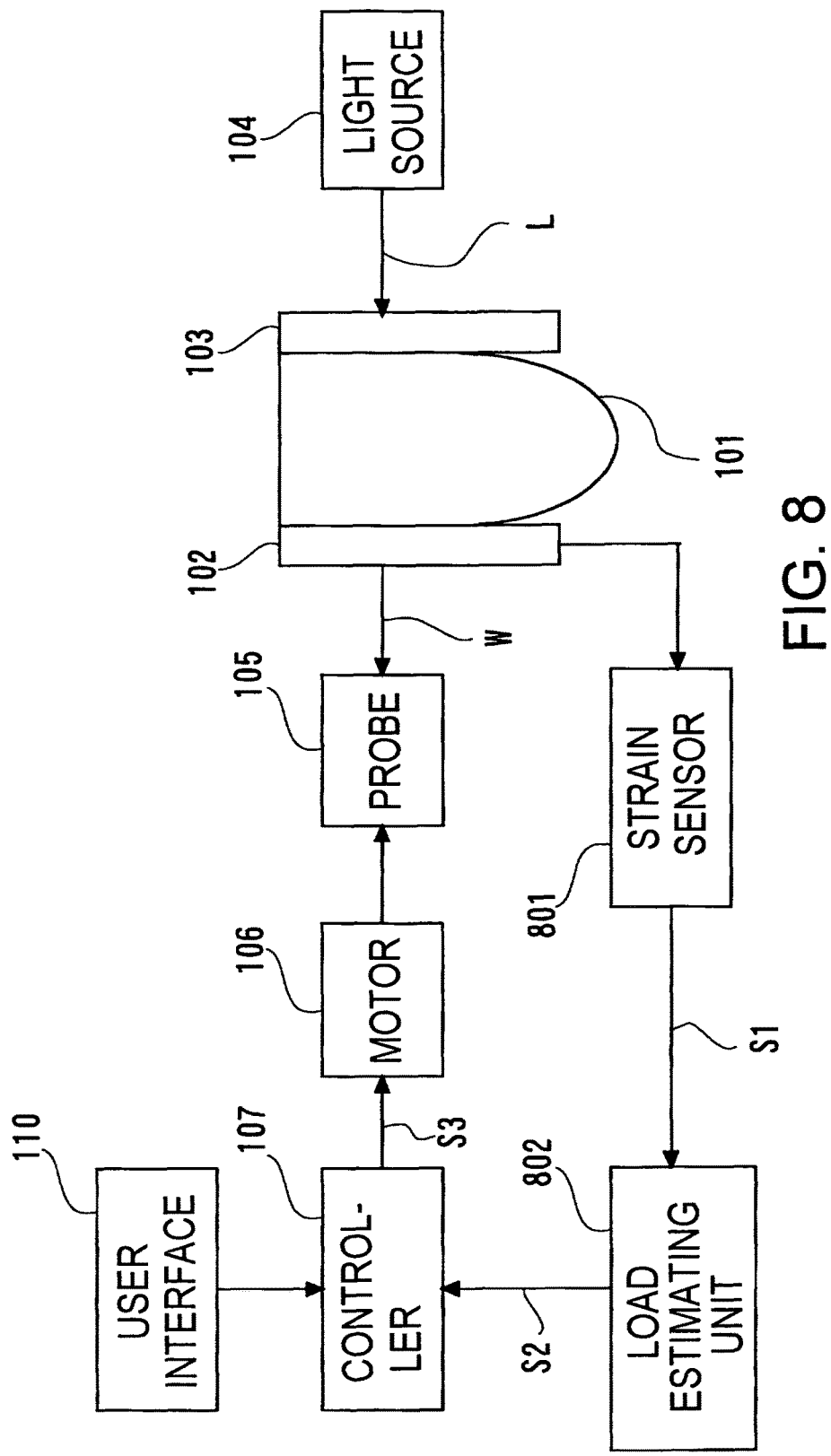
FIG. 8 is a block diagram of an elastic wave receiving apparatus according to a third embodiment of the invention.

FIG. 8 is a block configuration diagram showing a third embodiment of an elastic wave receiving apparatus according to the present invention. In the elastic wave receiving apparatus of the embodiment, to correct variations in a friction load caused by a strain in the compression plate 102 which occurs when the subject 101 is fixed to the compression plate 102, a strain sensor 801 as a strain detecting unit and a load estimating unit 802 as an information acquiring unit are provided. In FIG. 8, the subject 101, the compression plate 102, the compression plate 103, the light source 104, the probe 105, the motor 106, the controller 107, and the user interface 110 are similar to those in the first embodiment, so that their description will not be repeated.

Figure 9:
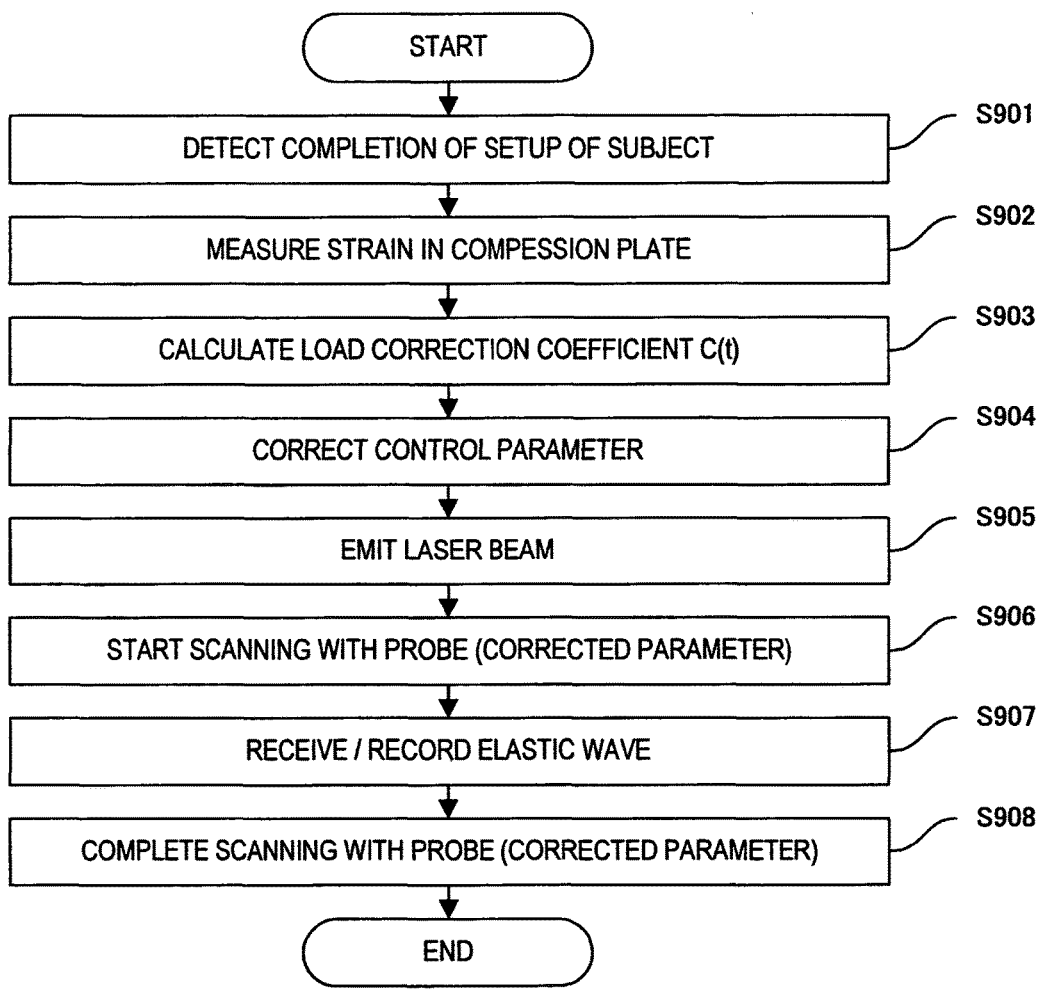
FIG. 9 is a flowchart showing a measurement flow according to the third embodiment of the invention.
Figure 10:
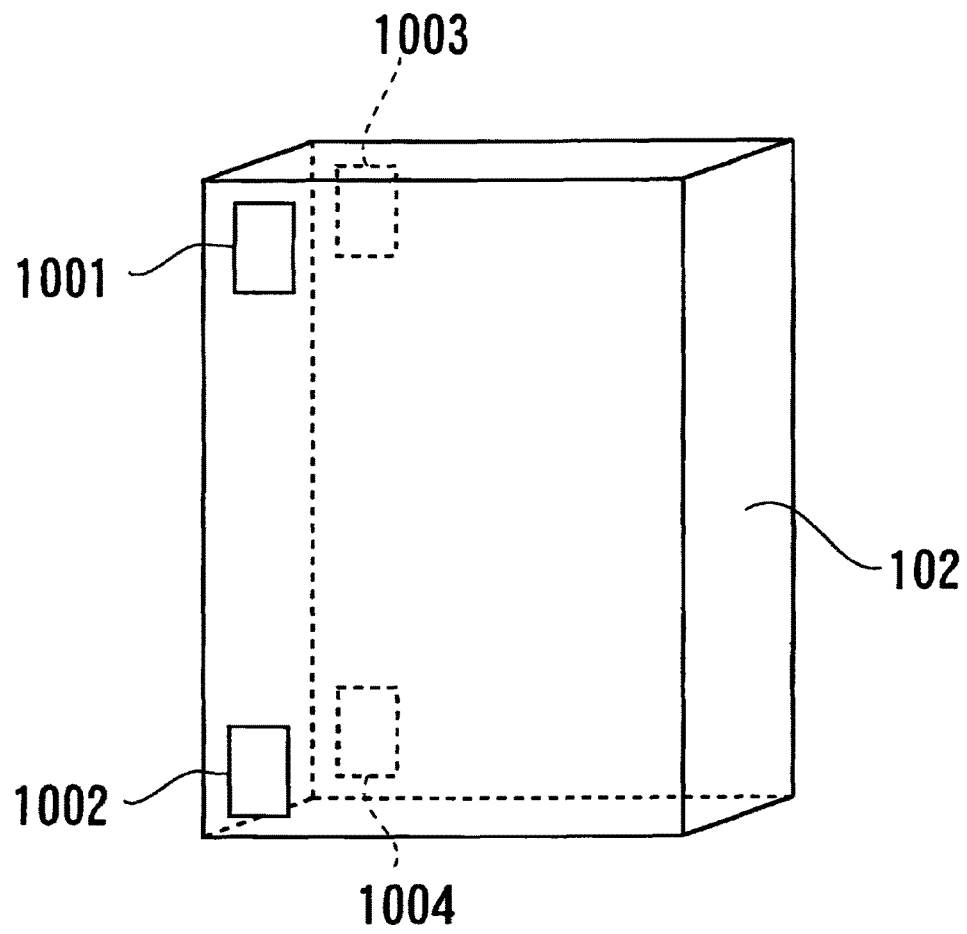
FIG. 10 is a diagram showing layout of strain gauges in the third embodiment of the invention.

FIG. 9 shows a measurement flow using the elastic wave receiving apparatus since the subject 101 in the third embodiment of the invention is fixed by the compression plates 102 and 103 until an elastic wave is received by the probe 105. In step S901, in a manner similar to the first and second embodiments, completion of setup of the subject 101 is detected. Next, in step S902, a strain in the compression plate 102 is measured by the strain sensor 801. The details of layout of the strain sensors 801 are shown in FIG. 10. Strain gauges 1001 and 1002 are adhered at both ends of a face on the probe 105 side, of the compression plate 102. Strain gauges 1003 and 1004 are adhered to both ends of a face on the subject 101 side. In step S902, the resistance value of each of the strain gauges is detected. In FIG. 10, this side of the drawing sheet is the face on the probe 105 side, and the depth side is the face on the subject 101 side.

Figure 11A:
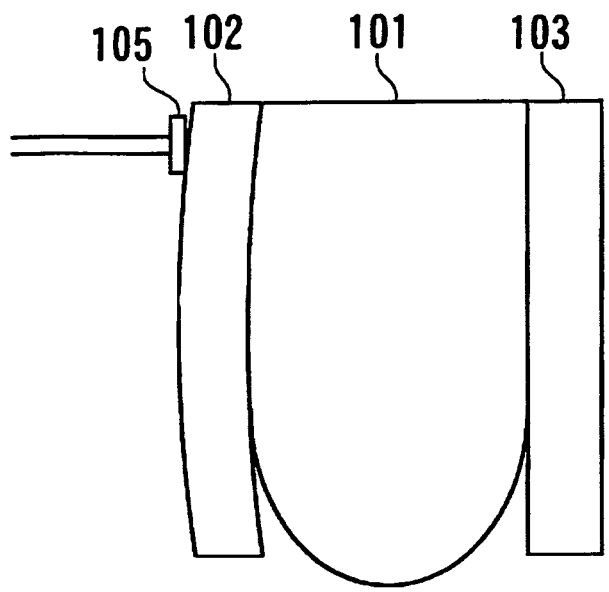
FIGS. 11A and 11B are diagrams showing example of a state of compression plates in the third embodiment of the invention.
Figure 11B:
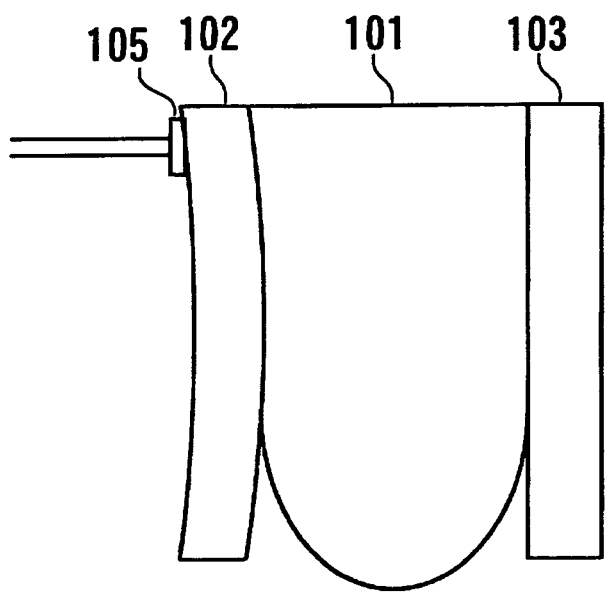

Subsequently, in step S903, the load estimating unit 802 estimates friction load at each position based on the resistance value of each of the strain gauges measured in step S902. The basic concept is as follows. Specifically, when the resistance values of the strain gauges 1001 and 1002 increase and the resistance values of the strain gauges 1003 and 1004 decrease, it is considered that the compression plate 102 is distorted so as to project to the probe side as shown in FIG. 11A. In this case, the frictional force between the probe 105 and the compression plate 102 is large around the center part of the compression plate 102 and is small around ends. On the other hand, when the resistance values of the strain gauges 1001 and 1002 decrease and the resistance values of the strain gauges 1003 and 1004 increase, it is considered that the compression plate 102 is distorted so that the probe 105 side is recessed as shown in FIG. 11B. In this case, the frictional force between the probe 105 and the compression plate 102 is small in a center part and becomes large around ends.

Next, a concrete method for estimating the friction load will be described. In the embodiment, as the load correction function C(t), the following quadratic function (5) is employed.

[Math. 5]

$$C(t) = A\left\{\left(f(t) - \frac{h}{2}\right)^2\right\} + B \qquad (5)$$

When A<0, B is defined as expression (6).

[Math. 6]

$$B = -A\frac{h^2}{4} \qquad (6)$$

When A≥0, B=0 is defined. "h" denotes length (height) from the lower end to the upper end of the compression plate 102 in FIGS. 11A and 11B.

A is defined by expression (7) and is a coefficient which becomes negative when the compression plate 102 is distorted so as to project to the probe side and becomes positive when the compression plate 102 is distorted so as to recess to the probe side. k denotes a positive constant which is determined at the time of shipping of the apparatus. The value of A is determined according to resistance values R1001, R1002, R1003, and R1004 of the strain gauges 1001, 1002, 1003, and 1004, respectively, detected in step S902 and is stored.

$$A = k\{(R1003 \cdot R1004)/(R1002 \cdot R1001) - 1\} \quad (7)$$

For example, in the case where the compression plate 102 is distorted so as to project to the probe side as shown in FIG. 11A, (R1002·R1001)>(R1003·R1004) is satisfied and, as a result, "A" becomes a negative value. In this case, C(t)=0 at ends (f(t)=0 and f(t)=h) of the compression plate 102, and the friction load is estimated small. C(t)=−A(h²/4) in the center (f(t)=h/2) of the compression plate 102, and the friction load is estimated large. For example, in the case where the compression plate 102 is distorted so as to recess as shown in FIG. 11B, (R1002·R1001)<(R1003·R1004) is satisfied and A becomes a positive value. In this case, C(t)=A(h²/4) at ends (f(t)=0 and f(t)=h) of the compression plate 102, and the friction load is estimated large. C(t)=0 in the center (f(t)=h/2) of the compression plate 102, and the friction load is estimated small. In the case where the compression plate 102 is not distorted, (R1002·R1001)=(R1003·R1004) and, as a result, A=B=0. In this case, C(t) is always equal to zero (C(t)=0).

Next, in step S904, the load estimating unit 802 changes the target position based on the load correction function C(t) and sets it in the controller 107. In the embodiment, a value obtained by adding the load correction function C(t) to the predetermined pulse input number N(t) is set as a corrected pulse input number N'(t). The controller 107 re-calculates the corrected pulse input number N'(t) at predetermined time intervals and updates the internal memory. Subsequently, in step S905, control of repeatedly emitting a pulse laser from the light source 104 in predetermined cycles is started. In step S906, the controller 107 starts driving the motor 106 and the probe 105 by using the corrected pulse input number N'(t). Concurrently, the light source 104 is also driven so as to face the probe 105 so that a photoacoustic wave generated on the inside of the subject 101 by the pulse laser beam can be received by the probe 105.

The operation of the probe 105 in the case where the compression plate 102 is distorted so as to project to the probe 105 side and the friction load is expected to be large around the center will now be considered. In this case, the controller 107 generates pulse signals more than the initial pulse input number N(t) around the center of the compression plate 102 based on the corrected pulse input number N'(t) so that the probe 105 can follow the target position f(t). On the other hand, in the case where it is expected that the compression plate 102 is distorted so as to recess and the friction load is large around the ends, the controller 107 generates pulse signals more than the initial pulse input number N(t) around the ends of the compression plate 102 based on the corrected pulse input number N'(t) so that the probe 105 can follow the target position f(t). Consequently, also in the case where the friction load changes in some place due to distortion of the compression plate 102, the position at each time, of the probe 105 can be made closer to the target position f(t).

Subsequently, in step S907, control of receiving a photoacoustic wave generated from the inside of the subject 101 by using the probe 105 and converting it to an electric signal is executed. The electric signal may be subjected to signal processing and imaging by another routine and an image may be displayed via the user interface 110. In step S908, the scan and measurement of an elastic wave of the probe 105 is finished. According to the third embodiment of the invention, fluctuations in the friction load accompanying distortion of the compression plate 102 can be corrected by a simple method without making the probe 105 scan before measurement. Consequently, without increasing the measurement time, the load fluctuations accompanying distortion of the compression plate 102 are corrected, and the position precision of the probe 105 can be improved. In the measurement flow, the process in step S902 corresponds to the information acquiring step. The processes in steps S903 and S904 correspond to the instruction signal correcting step. Further, the processes in steps S906 to S908 correspond to the driving step. The pulse input number N(t) corresponds to an instruction signal.

Although the quadratic function expressed by the expression (5) is used as the load correction function C(t) in the above example, the load correction function C(t) is not always limited to the expression. Another function which changes according to a measurement value of a strain gauge may be used. Although the expression in which the pulse input number N(t) before correction and the load correction function C(t) are added is used as the corrected pulse input number N'(t) in the embodiment, the invention is not always limited to the expression. Another function which changes according to the value of the load correction function C(t) may be used. In the embodiment, the method in which the acceleration start time is the same regardless of the load correction function C(t) has been described. However, the acceleration start time may be also changed together with a change in the number of input pulses. For example, in the case where the load is estimated large, a driving method is changed so as to increase the pulse input number and hasten the timing (increase the drive speed and hasten the drive timing (or increase the movement speed and hasten the moving timing)). In such a manner, the probe 105 can be moved to a target position well in advance of generation of a photoacoustic wave. On the other hand, for example, in the case where the load is estimated small, a driving method is changed so as to decrease the pulse input number and delay the timing (decrease the drive speed and delay the drive timing (or decrease the movement speed and delay the moving timing)). In such a manner, the probe 105 can be moved to a target position. In the embodiment, the distortion of the compression plate 102 corresponds to a physical value corresponding to the load generated in the driving unit.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-284541, filed on Dec. 15, 2009, which is hereby incorporated by reference herein its entirety.

The invention claimed is:

1. An acoustic wave receiving apparatus comprising:
a supporting member configured to support a subject;
a scanning light source located opposing the subject via the supporting member and configured to irradiate the subject with pulsed light so as to generate a photoacoustic wave at the subject;
a scanning probe acoustically and slidably in contact with the supporting member via an acoustic impedance matching agent and configured to receive an acoustic wave propagated from the subject via the supporting member and output an electric signal in response to receipt of the photoacoustic wave;
a driving unit configured to move said scanning probe and said scanning light source along the supporting member;
a drive controlling unit that supplies a drive signal to said driving unit such that said scanning probe is moved; and
an information acquiring unit configured to, preliminary to acquiring data from the subject, acquire and store a physical value corresponding to a load generated due to an acoustic connection between the scanning probe and the supporting member,
wherein said drive controlling unit corrects the drive signal by using the physical value stored in said information acquiring unit to correct for a scanning inaccuracy due to the load such that said scanning probe moves in association with a position of the scanning light source, simultaneously.

2. The acoustic wave receiving apparatus according to claim 1, wherein said information acquiring unit has a position detecting unit that detects a position of said scanning probe, said scanning of the scanning probe is performed in advance, and the difference between a position of said scanning probe detected and the predetermined target position is stored in said information acquiring unit as a physical value corresponding to the scanning load.

3. The acoustic wave receiving apparatus according to claim 2, wherein, at the time of acquiring the physical value, said scanning of the scanning probe is performed in a state in which no acoustic wave is generated from the subject.

4. The acoustic wave receiving apparatus according to claim 2, wherein, when the scanning load corresponding to the physical value is larger than a scanning load which is assumed from the predetermined target position, said information acquiring unit increases driving speed or hastens drive timing of said scanning probe.

5. The acoustic wave receiving apparatus according to claim 2, wherein, when the scanning load corresponding to the physical value is smaller than a scanning load which is assumed from the predetermined target position, said information acquiring unit decreases driving speed or delays drive timing of said scanning probe.

6. The acoustic wave receiving apparatus according to claim 1, wherein said information acquiring unit has a temperature detecting unit that detects a temperature of said supporting member, and the detected temperature is stored in said information acquiring unit as a physical value corresponding to the scanning load.

7. The acoustic wave receiving apparatus according to claim 6, wherein said information acquiring unit stores information regarding viscosity of a matching agent applied to the supporting member as a physical value corresponding to the scanning load.

8. The acoustic wave receiving apparatus according to claim 1, wherein said information acquiring unit has a strain detecting unit that detects a strain in said supporting member, and the strain detected is stored as a physical value corresponding to the scanning load in said information acquiring unit.

9. The acoustic wave receiving apparatus according to claim 1, wherein the scanning probe is slidably contacted with the supporting member via an acoustic impedance matching agent.

10. The acoustic wave receiving apparatus according to claim 1, wherein the physical value corresponding to the scanning load is acquired by at least any one of measurement and calculation.

11. The acoustic wave receiving apparatus according to claim 1, wherein said information acquiring unit acquires and stores the physical value before the photoacoustic wave is received by the scanning probe.

12. The acoustic wave receiving apparatus according to claim 1, wherein said drive controlling unit corrects the drive signal before the photoacoustic wave is received by the scanning probe.

13. An acoustic wave receiving method for an acoustic wave receiving apparatus including a supporting member, a scanning light source and a scanning probe, comprising:
supporting a subject with the supporting member;
estimating a scanning load occurring between the scanning probe and the supporting member;
correcting a scanning instruction signal by using a physical value to correct for a scanning inaccuracy due to the scanning load;
irradiating the subject with a pulsed light by using the scanning light source;
receiving a photoacoustic wave generated in the subject in response to the irradiation of the subject with the pulsed light by using the scanning probe; and
moving the scanning probe and the scanning light source,
wherein the irradiating the subject with the pulsed light and the receiving the photoacoustic wave are performed simultaneously during the moving the scanning probe by using the corrected instruction signal such that a common region of interest is irradiated with pulsed light and the scanning probe receives the photoacoustic wave propagated from that common region.

14. The acoustic wave receiving method according to claim 13, wherein, in said information acquiring step, the physical value is acquired by making the scanning probe scan over the supporting member in a state where no acoustic wave is generated from the subject.

15. The acoustic wave receiving method according to claim 13, wherein, in said information acquiring step, position information of the scanning probe is acquired as a physical value corresponding to the scanning load by making the scanning probe scan over the supporting member, and the difference between acquired position information and the target position of the scanning probe is calculated, and
in said instruction signal correcting step, movement speed or movement timing of the scanning probe is changed so as to decrease the difference between the position of the scanning probe and the target position.

16. The acoustic wave receiving method according to claim 13, wherein, in said information acquiring step, a temperature of the supporting member is acquired as the physical value corresponding to the scanning load.

17. The acoustic wave receiving method according to claim 13, wherein, in said information acquiring step, a strain of the supporting member is acquired as the physical value corresponding to the scanning load.

18. The acoustic wave receiving method according to claim 13, wherein, in said instruction signal correcting step, in a case in which the scanning load corresponding to the physical value acquired in the information acquiring step is larger than a scanning load which is assumed from the target position, the instruction signal is corrected so that drive speed or drive timing of the scanning probe is increased or hastened.

19. The acoustic wave receiving method according to claim 13, wherein, in said instruction signal correcting step, when the scanning load corresponding to the physical value acquired in the information acquiring step is smaller than a scanning load which is assumed from the target position, the instruction signal is corrected so that drive speed or drive timing of the scanning probe is decreased or delayed.

20. A non-transitory computer-readable medium, storing, in executable form, a program for making a computer execute an information acquiring step, an instruction signal correcting step, and a drive step in the acoustic wave receiving method according to claim 13.

21. The acoustic wave receiving method according to claim 13, wherein the estimating is performed before the scanning.

22. The acoustic wave receiving method according to claim 13, wherein the estimating is performed before the irradiating the subject with the pulsed light and the receiving the photoacoustic wave.

23. The acoustic wave receiving method according to claim 13, wherein the estimating is performed before the irradiating the subject with the pulsed light and the receiving the photoacoustic wave.

24. The acoustic wave receiving method according to claim 13, wherein the physical value corresponding to the scanning load is acquired by at least any one of measurement and calculation.

* * * * *